(12) United States Patent
Han et al.

(10) Patent No.: US 9,181,592 B2
(45) Date of Patent: Nov. 10, 2015

(54) METHOD FOR DETECTING A BACTERIAL PATHOGEN

(75) Inventors: Yiping W. Han, Beachwood, OH (US); Akihiko Ikegami, Ibaraki (JP)

(73) Assignee: Case Western Reserve University, Cleveland, OH (US)

( * ) Notice: Subject to any disclaimer, the term of this patent is extended or adjusted under 35 U.S.C. 154(b) by 227 days.

(21) Appl. No.: 12/056,633

(22) Filed: Mar. 27, 2008

(65) Prior Publication Data

US 2009/0081656 A1    Mar. 26, 2009

Related U.S. Application Data

(60) Provisional application No. 60/908,992, filed on Mar. 30, 2007.

(51) Int. Cl.
*C12Q 1/68* (2006.01)
*C12Q 1/04* (2006.01)

(52) U.S. Cl.
CPC . *C12Q 1/689* (2013.01); *C12Q 1/04* (2013.01)

(58) Field of Classification Search
None
See application file for complete search history.

(56) References Cited

U.S. PATENT DOCUMENTS 6,150,517 A * 11/2000 Hogan et al. ............. 536/25.3

FOREIGN PATENT DOCUMENTS

| WO | WO 9932603 A1 | * | 7/1999 |
| WO | WO 03016510 A1 | * | 2/2003 |
| WO | WO 2005112993 A1 | * | 12/2005 |

OTHER PUBLICATIONS

Bearfield et al., "Possible association between amniotic fluid microorganism infection and microflora in the mouth," BJOG: an International Journal of Obstetrics and Gynaecology, May 2002, vol. 109, pp. 527-533.*
Osorio et al., "16S rRNA Gene Sequence Analysis of *Photobacterium damselae* and Nested PCR Method for Rapid Detection of the Causative Agent of Fish Pasteurellosis," Applied and Environmental Microbiology, Jul. 1999, vol. 65, No. 7, pp. 2942-2946.*
Han et al., "Transmission of an Uncultivated *Bergeyella* Strain from the Oral Cavity to Amniotic Fluid in a Case of Preterm Birth," Journal of Clinical Microbiology, Apr. 2006, vol. 44, No. 4, pp. 1475-1483.*
GenBank Accession No. A02070, Mar. 1993.*
GenBank Accession No. A25714, Mar. 1995.*

(Continued)

*Primary Examiner* — Young J Kim
(74) *Attorney, Agent, or Firm* — Tarolli, Sundheim, Covell & Tummino LLP

(57) ABSTRACT

A method is provided for detecting a bacterial pathogen in a sample. One step of the method includes obtaining a sample and then subjecting the sample to nested PCR. The nested PCR is conducted in the presence of at least two outer oligonucleotide primers complementary to a target nucleotide sequence of the bacterial pathogen so that a first amplified product is produced. The target nucleotide sequence includes at least a portion of a 16S-23S ribosomal RNA sequence. The first amplified product is subjected to the nested PCR in the presence of at least two inner oligonucleotide primers complementary to the nucleotide sequence of the first amplified product so that a second amplified product is obtained. Detection of the second amplified product indicates the presence of the bacterial pathogen in the sample.

7 Claims, 5 Drawing Sheets

(56) References Cited

OTHER PUBLICATIONS

Berridge et al., "Development of Specific Nested Oligonucleotide PCR Primers for the *Streptococcus iniae* 16S-23S Ribosomal DNA Intergenic Spacer," Journal of Clinical Microbiology, Sep. 1998, vol. 36, No. 9, pp. 2778-2781.*

Hinrikson et al., "Detection of three different types of '*Tropheryma whippelii*' directly from clinical specimens by sequencing, single-strand conformation polymorphism (SSCP) analysis and type-specific PCR of their 16S-23S ribosomal intergenic spacer region," International Journal of Systematic Bacteriology, 1999, vol. 49, pp. 1701-1706.*

Hinrikson et al., "Detection of three different types of '*Tropheryma whippelii*' directly from clinical specimens by sequencing, single-stranded conformation polymorphism (SSCP) analysis and type-specific PCR of their 16S-23S ribosomal intergenic spacer region," Int'l. J. of System. Bact., 1999, vol. 49, pp. 1701-1706.*

* cited by examiner

METHOD FOR DETECTING A BACTERIAL PATHOGEN

RELATED APPLICATION

This application claims priority from U.S. Provisional Application No. 60/908,992, filed Mar. 30, 2007, the subject matter, which is incorporated herein by reference.

GOVERNMENT FUNDING

This invention was made with government support under Grant No. DE014447 awarded by National Institutes of Health, National Institute of Dental and Craniofacial Research. The government has certain rights in the invention.

TECHNICAL FIELD

The present invention relates generally to a method and kit for detecting and identifying pathogens, and more particularly to a method and kit for detecting and identifying bacterial pathogens in a sample.

BACKGROUND OF THE INVENTION

Preterm birth (PTB) is a significant public health problem and accounts for approximately 11% of all deliveries in the United States. It is the leading cause of prenatal death, and the surviving infants may encounter long-term health problems throughout their lives. The majority of this morbidity and mortality involves a small subset of infants born before 30 to 32 weeks of gestation. Although advancement in medical technology has steadily improved the survival rate of the preterm infants, the PTB rate has not improved during the past 4 decades, showing instead a slight upward trend. Thus, identification of new risk factors for PTB could have significant social and economic impact.

Periodontal disease is one of the newly identified risk factors for PTB. Epidemiologic and intervention studies have indicated a link between these two conditions. However, contradictory reports also exists. The questions of whether periodontal disease is a risk factor for PTB and what is the mechanism underlying the potential link remain. Animal studies have provided evidence supporting the potential link and have suggested two possible mechanisms. One mechanism suggest that periodontal disease could lead to systemic dissemination of inflammatory mediators and/or periodontal pathogens causing adverse pregnancy outcomes. The other mechanism suggests that oral bacteria may translocate specifically into the pregnant uterus and induce adverse pregnancy outcomes due to localized infection.

One of the known causes of PTB is intrauterine infection. The infection rate is inversely related to the gestational age. The paradigm has been that intrauterine infections most commonly originate from the lower genital tract and that the microorganisms invade the pregnant uterus through an ascending mechanism. A less common route of infection is hematogenous transmission, where the infectious organism may originate from other parts of the body. As one of the major microbial habitats in the human body, hosting as many as 700 different species, the oral cavity is a potential microbial reservoir for infection. Indeed, organisms with an oral origin such as *Fusobacterium nucleatum* and *Capnocytophaga* spp., have been associated with intrauterine infections, with *F. nucleatum* being one of the most frequently cultivated from or detected in the infected uterus. However, direct evidence detecting and matching the microorganisms in intrauterine infections with those in the oral cavities of the pregnant women is lacking.

SUMMARY OF THE INVENTION

The present invention relates generally to a method and kit for detecting and identifying pathogens, and more particularly to a method and kit for detecting and identifying bacterial pathogens in a bodily sample.

According to an aspect of the present invention, a method is provided for detecting a bacterial pathogen in a sample. One step of the method includes obtaining a sample and then subjecting the sample to nested PCR. The nested PCR is conducted in the presence of at least two outer oligonucleotide primers complementary to a target nucleotide sequence of the bacterial pathogen so that a first amplified product is produced. The target nucleotide sequence comprises at least a portion of a 16S-23S ribosomal RNA sequence. The first amplified product is subjected to the nested PCR in the presence of at least two inner oligonucleotide primers complementary to the nucleotide sequence of the first amplified product so that a second amplified product is obtained. Detection of the second amplified product indicates the presence of the bacterial pathogen in the sample.

According to another aspect of the present invention, a method for detecting a bacterial pathogen in amniotic fluid is provided. One step of the method includes obtaining a sample of the amniotic fluid and then subjecting the sample to nested PCR. The nested PCR is conducted in the presence of at least two outer oligonucleotide primers complementary to a target nucleotide sequence of the bacterial pathogen so that a first amplified product is produced. The target nucleotide sequence comprises at least a portion of a 16S-23S ribosomal RNA sequence. The first amplified product is subjected to the nested PCR in the presence of at least two inner oligonucleotide primers complementary to the nucleotide sequence of the first amplified product so that a second amplified product is obtained. Detection of the second amplified product indicates the presence of the bacterial pathogen in the sample.

According to another aspect of the present invention, a method is provided for detecting a bacterial pathogen in amniotic fluid. One step of the method includes obtaining a sample of the amniotic fluid and subjecting the sample to nested PCR. The nested PCR is conducted in the presence of at least two outer oligonucleotide primers complementary to a target nucleotide sequence of the bacterial pathogen so that a first amplified product is produced. The at least two outer oligonucleotide primers are selected from the group consisting of 5'-GGATTAGATACCCTGGTAGTC-3' (SEQ ID NO:1) and 5'-GGAGTATTTAGCCTT-3' (SEQ ID NO:2). The first amplified product is subjected to the nested PCR in the presence of at least two inner oligonucleotide primers complementary to the nucleotide sequence of the first amplified product so that a second amplified product is obtained. The at least two inner oligonucleotide primers are selected from the group consisting of 5'-GGATTAGATACCCTGG-TAGTC-3' (SEQ ID NO:1), 5'-GTTTGATCCTGGCTCAG-3' (SEQ ID NO:3), 5'-GGTACTTAGATGTTTCAGTTC-3' (SEQ ID NO:4), and 5'-(G/T)TTCGCTCGCC(A/G)CTAC-3' (SEQ ID NO:5). Detection of the second amplified product indicates the presence of the bacterial pathogen in the sample.

According to another aspect of the present invention, a kit for detecting a bacterial pathogen in a sample is provided. The kit comprises at least two outer oligonucleotide primers complementary to a target nucleotide sequence comprising at least a portion of a 16S-23S ribosomal RNA sequence of the bacterial pathogen. The at least two outer oligonucleotide primers are used to obtain a first amplified product in a nested PCR. The kit also includes at least two inner oligonucleotide primers complementary to the nucleic acid sequence of the first amplified product. The at least two inner oligonucleotide primers are used to obtain a second amplified product in a nested PCR.

BRIEF DESCRIPTION OF THE DRAWINGS

The foregoing and other features of the present invention will become apparent to those skilled in the art to which the present invention relates upon reading the following description with reference to the accompanying drawings, in which:

FIG. 4A is a PCR using universal primers 785F and 442R. The products obtained were used as templates for nested PCR in FIGS. 4B-E. FIG. 4B shows nested PCR using universal primers 785F and L189R. FIG. 4C shows nested PCR using Bergeyella-specific primer BergF and universal primer L189R. FIG. 4D shows nested PCR using Bergeyella-specific primers BergF and 14 BitsR1. FIG. 4E shows nested PCR using Bergeyella-specific primers BergF and 14 BitsR2. Lanes M, molecular size markers, as indicated on the left. Lanes A, AF. Lanes P, subgingival plaque. Lanes V, vaginal swab.

DETAILED DESCRIPTION

Figure 1:
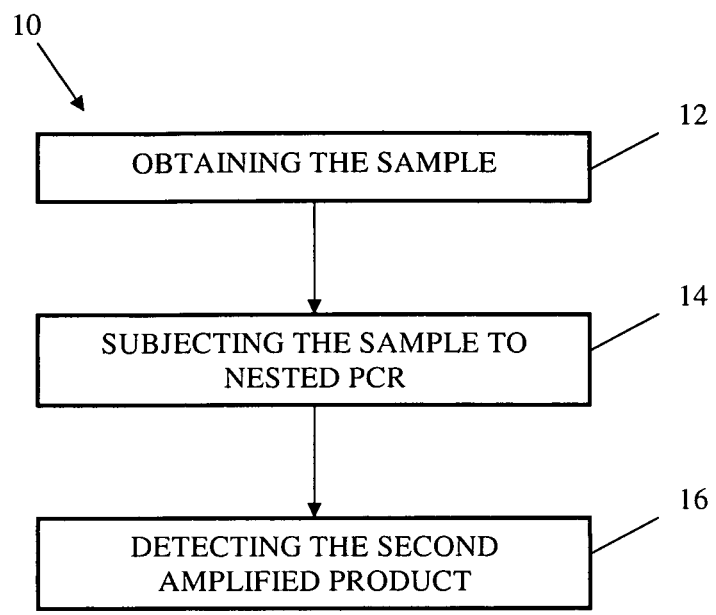
FIG. 1 is a flow diagram illustrating a method for detecting a bacterial pathogen according to the present invention.

The present invention relates generally to a method and kit for detecting and identifying pathogens, and more particularly to a method and kit for detecting and identifying bacterial pathogens in a sample. The present invention is based on the discovery that nested PCR and DNA fingerprinting facilitated detection and identification of uncultivated bacterial pathogens in amniotic fluid, while Gram-stain and culturing methods failed to detect the pathogens. More particularly, the present invention is based on the discovery that a set of universal primers complementary to a specific portion of the 16S-23S ribosomal RNA (rRNA) sequence of a bacterial pathogen can be used with nested PCR and DNA fingerprinting to detect and identify uncultured bacterial pathogens. Based on these discoveries, the present invention provides a method for detecting a bacterial pathogen in a sample, a method for detecting a bacterial pathogen in amniotic fluid, and a kit for detecting a bacterial pathogen in a sample.

Methods involving conventional molecular biology techniques are described herein. Such techniques are generally known in the art and are described in detail in methodology treatises, such as Current Protocols in Molecular Biology, ed. Ausubel et al., Greene Publishing and Wiley-Interscience, New York, 1992 (with periodic updates). Unless otherwise defined, all technical terms used herein have the same meaning as commonly understood by one of ordinary skill in the art to which the present invention pertains. Commonly understood definitions of molecular biology terms can be found in, for example, Rieger et al., Glossary of Genetics: Classical and Molecular, 5th Edition, Springer-Verlag: New York, 1991, and Lewin, Genes V, Oxford University Press: New York, 1994.

The definitions provided herein are to facilitate understanding of certain terms used frequently herein and are not meant to limit the scope of the present invention.

In the context of the present invention, the terms "complementary" and "substantially complementary" refer to the hybridization, base pairing, or duplex formation between nucleotides or nucleic acids, such as, for instance, between the two strands of a double-stranded DNA molecule or between an oligonucleotide primer and a primer binding site on a single-stranded nucleic acid. Complementary nucleotides are, generally, A and T (or A and U), or C and G. Two single-stranded RNA or DNA molecules are said to be substantially complementary when the nucleotides of one strand, optimally aligned and compared with appropriate nucleotide insertions or deletions, pair with at least about 80% of the nucleotides of the other strand, usually at least about 90% to 95%, and more preferably from about 98 to 100%. Alternatively, substantial complementarity exists when an RNA or DNA strand will hybridize under selective hybridization conditions to its complement. For example, selective hybridization may occur when there is at least about 65% complementary over a stretch of at least 14 to 25 nucleotides, preferably at least about 75%, and more preferably at least about 90% complementary.

As used herein, the term "fragment" refers to a sub-sequence of a nucleic acid that is of a sufficient size and confirmation to properly function as a hybridization probe, as a primer in a PCR, or in another manner characteristic of nucleic acids.

As used herein, the term "hybridization" refers to the formation of a duplex structure by two single-stranded nucleic acids due to fully (100%) or less than fully (less than 100%) complementary base pairing. Hybridization can occur between fully and complementary nucleic acid strands, or between less than fully complementary nucleic acid strands which contain regions of mismatch due to one or more nucleotide substitutions, deletions, or additions.

As used herein, the term "kit" refers to any delivery system for delivering materials or reagents for carrying out a method of the present invention. In the context of assays, such delivery systems include systems that allow for the storage, transport, or delivery of reaction reagents (e.g., probes, enzymes, etc. in the appropriate containers) and/or supporting materials (e.g., buffers, written instructions for performing the assay etc.) from one location to another. For example, kits can include one or more enclosures (e.g., boxes) containing the relevant reaction reagents and/or supporting materials for assays of the present invention.

As used herein, the term "oligonucleotide" refers to a linear polymer of nucleotide monomers. Monomers making up oligonucleotides are capable of specifically binding to a natural polynucleotide by way of a regular pattern of monomer-to-monomer interactions, such as Watson-Crick type of base pairing, base stacking, Hoogsteen or reverse Hoogsteen types of base pairing, or the like. Such monomers and their internucleosidie linkages may be naturally occurring or may be analogs thereof, e.g., naturally occurring or non-naturally occurring analogs. Non-naturally occurring analogs may include PNAs, phosphorothioate internucleosidie linkages, bases containing linking groups permitting the attachment of labels, such as fluorophores, or haptens, and the like. Whenever the use of an oligonucleotide requires enzymatic processing, such as extension by a polymerase, ligation by a ligase, or the like, one of ordinary skill would understand that oligonucleotides in those instances would not contain certain analogs of internucleosidic linkages, sugar moities, or bases at any or some positions. Polynucleotides typically range in size from a few monomeric units, e.g., 5-40, when they are usually referred to as "oligonucleotides," to several thousand monomeric units. Whenever an oligonucleotide is represented by a sequence of letters (upper or lower case), such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, "I" denotes deoxyinosine, "U" denotes uridine, unless otherwise indicated or obvious from context.

As used herein, the term "PCR" refers to a reaction for the in vitro amplification of specific DNA sequences by the simultaneous primer extension of complementary strands of DNA. In other words, PCR is a reaction for making multiple copies or replicates of a target nucleotide sequence flanked by primer binding sites. PCR typically comprises one or more repetitions of the following steps: (i) denaturing a target nucleotide sequence; (ii) annealing primers to primer binding sites; and (iii) extending the primers by a nucleic acid polymerase in the presence of nucleoside triphosphates. Usually, the reaction is cycled through different temperatures optimized for each step in a thermal cycler instrument. Particular temperatures, durations at each step, and rates of change between steps depend on many factors well-known to those of ordinary skill in the art. For example, in a conventional PCR using Taq DNA polymerase, a double-stranded target nucleotide sequence may be denatured at a temperature >90° C., primers annealed at a temperature in the range 50-75° C., and primers extended at a temperature in the range 72-78° C. Reaction volumes range from a few hundred nanoliters, e.g., 200 nl, to a few hundred µl, e.g., 200 µl. The term "PCR" encompasses derivative forms of the reaction, including but not limited to, RT-PCR, real-time PCR, nested PCR, quantitative PCR, multiplexed PCR, and the like.

As used herein, the term "reverse transcription PCR," or "RT-PCR," refers to a PCR that is preceded by a reverse transcription reaction that converts a target RNA to a complementary single stranded DNA, which is then amplified.

As used herein, the term "real-time PCR" refers to a PCR for which the amount of reaction product is monitored as the reaction proceeds. There are many forms of real-time PCR that differ mainly in the detection chemistries used for monitoring the reaction product.

As used herein, the term "nested PCR" refers to a two-stage PCR wherein the amplified product of a first PCR becomes the sample for a second PCR using a new set of primers, at least one of which binds to an interior location of the first reaction product. "Outer primers" in reference to a nested amplification reaction refer to the primers used to generate a first reaction product, and "inner primers" refer to the one or more primers used to generate a second, or nested, reaction product.

As used herein, the term "multiplexed PCR" refers to a PCR wherein multiple target sequences (or a single target sequence and one or more reference sequences) are simultaneously carried out in the same reaction mixture. Usually, distinct sets of primers are employed for each sequence being amplified.

As used herein, the term "quantitative PCR" refers to a PCR designed to measure the abundance of one or more specific target sequences in a sample or specimen. Quantitative PCR includes both absolute quantitation and relative quantitation of such target sequences. Quantitative measurements are made using one or more reference sequences that may be assayed separately or together with a target sequence. The reference sequence may be endogenous or exogenous to a sample or specimen, and in the latter case, may comprise one or more competitor templates.

As used herein, the term "primer" refers to an oligonucleotide, either natural or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension process are determined by the sequence of the template polynucleotide. Usually primers are extended by a DNA polymerase. Primers usually have a length in the range of from 14 to 36 nucleotides.

As used herein, the term "sample" refers to a quantity of material from a biological, medical, or subject source in which detection or measurement of target nucleotide sequence is sought. On the one hand, the term is meant to include a specimen or culture (e.g., microbiological cultures). On the other hand, it is meant to include biological samples. A sample may include a specimen of synthetic origin. Biological samples may be animal, including human, fluid, solid (e.g., stool) or tissue. Biological samples may also include materials taken from a subject including, but not limited to, cultures, blood, saliva, cerebral spinal fluid, amniotic fluid, pleural fluid, milk, lymph, sputum, semen, needle aspirates, and the like. These examples are not to be construed as limiting the sample types applicable to the present invention.

As used herein, the term "target nucleotide sequence" refers to a region of a nucleotide which is to be amplified, detected, or otherwise analyzed. An oligonucleotide primer hybridizes to a region of the polynucleotide template immediately flanking the target nucleotide sequence.

FIG. 1 is a flow diagram illustrating an aspect of the present invention. In FIG. 1, a method 10 for detecting a bacterial pathogen in a sample is provided. Bacterial pathogens can include any Gram-positive or Gram-negative bacteria capable of causing a disease, disorder, or other unwanted condition in a subject. One having ordinary skill in the art will appreciate the range and diversity of bacterial pathogens and understand that any one or combination of known bacterial pathogens may be detected using the method 10 of the present invention.

At 20, a sample may be obtained from a subject. As used herein, the term "subject" refers to any warm-blooded animal, preferably mammals, including humans. The sample can include a quantity of material from a biological, medical, or subject source in which detection or measurement of a target nucleotide sequence is sought. On the one hand, the term is meant to include a specimen or culture (e.g., microbiological cultures). On the other hand, it is meant to include biological samples. A sample may include a specimen of synthetic origin. Biological samples may be animal, including human, fluid, solid (e.g., stool) or tissue. Biological samples may also include materials taken from a subject including, but not limited to cultures, blood, saliva, cerebral spinal fluid, amniotic fluid, pleural fluid, milk, lymph, sputum, semen, needle aspirates, and the like. Methods for obtaining samples, such as by biopsy, syringe, or amniocentesis are known in the art.

After obtaining the sample at 20, DNA (or RNA) from a bacterial pathogen, if present, can be at least partially extracted and purified. Methods for extracting and purifying DNA are known in the art and include, for example, liquid-liquid extraction techniques. One such liquid-liquid extraction technique includes phenol-chloroform extraction. Phenol-chloroform extraction may be used to purify DNA contaminated by histones and other proteins. Typically, equal volumes of a phenol:chloroform mixture and the aqueous DNA sample are mixed, forming a biphasic mixture. The proteins will partition into the organic phase while the DNA (as well as other contaminants such as salts, sugars, etc.) remain in the aqueous phase. This is usually repeated at least once and then followed by precipitation with ethanol or isopropanol, for example. Other techniques (and commercially available kits) for DNA extraction are known in the art and include, for example, phenol:chloroform extraction followed by a cetyltrimethylammonium bromide precipitation step, silica-gel columns, and magnetic glass particles.

In an example of the method 10, a sample of amniotic fluid may be obtained at 12 from a subject using amniocentesis. The subject may be pregnant, for example, and may have at least one indicia of bacterial infection, such as inflammation of the uterus. Following amniocentesis, amniotic fluid may be placed directly into sterile 15-ml centrifuge tubes. The samples may then be divided into about 1 ml aliquots and the centrifuged at 10,000×g for about 3 minutes. Next, the supernatants from each of the samples may be removed and the pellets stored at about −80° C.

Each frozen pellet may then be suspended in about 500 µl lysis buffer (about 50 mM Tris-HCl, about pH 8.0, about 500 mM NaCl, about 50 mM EDTA, and about 1% sodium dodecyl sulfate) containing about 150 mg of 0.1-mm and 50 mg of 0.5-mm zirconia/silica beads. Samples may be vigorously mixed for about 3 minutes by vortexing and then incubated at about 70° C. for about 15 minutes. After centrifugation at 10,000×g for about 5 minutes, the supernatant can be collected and mixed with about 130 µl of about 10M ammonium acetate. The mixture may then be incubated on ice for about 5 minutes and centrifuged at 10,000×g for about 10 minutes. DNA may then be isolated from the supernatant by isopropanol precipitation, purified using a commercial kit (e.g., GENECLEAN TURBO kit (Qbiogene, Irvine, Calif.)), and suspended in about 30 µl of elution solution from the kit.

At 14, the sample containing at least partially purified DNA may be subjected to nested PCR. In general, nested PCR is a variation of PCR in that two pairs of PCR primers are used to amplify a target nucleotide sequence. The first outer pair of primers amplifies a target nucleotide sequence similar to a standard PCR. However, a second pair of inner primers (also known as nested primers) binds inside the first amplified PCR product to allow amplification of a second PCR product which is shorter than the first one. The advantage of nested PCR is that if the wrong target nucleotide sequence was initially amplified, the probability is quite low that the region would be amplified a second time by the second set of primers. Thus, nested PCR is a very specific PCR amplification.

In one aspect of the present invention, a nested PCR reaction may be prepared using at least partially purified DNA extracted from the sample. The nested PCR may be conducted in the presence of at least two outer oligonucleotide primers complementary or substantially complementary to a target nucleotide sequence of the bacterial pathogen so that a first amplified product is produced. The DNA region between the 16S and 23S rRNA genes in bacteria (i.e., the intergene region, IGR) is variable in length, and there are highly conserved sequences on each side (i.e., the 5'-end of the 16S rRNA gene and the 3'-end of the 23S rRNA gene). Another feature of the 16S-23S rRNA gene IGR is that there are usually several copies of this region in a single bacterium and there is usually size variability even within the same organism. Based on the characteristics of the 16S-23S rRNA gene, the target nucleotide sequence of the present invention can comprise at least a portion of a 16S-23S rRNA sequence. Alternatively, the target nucleotide sequence can comprise at least a portion of a 16S rRNA sequence.

Figure 2:
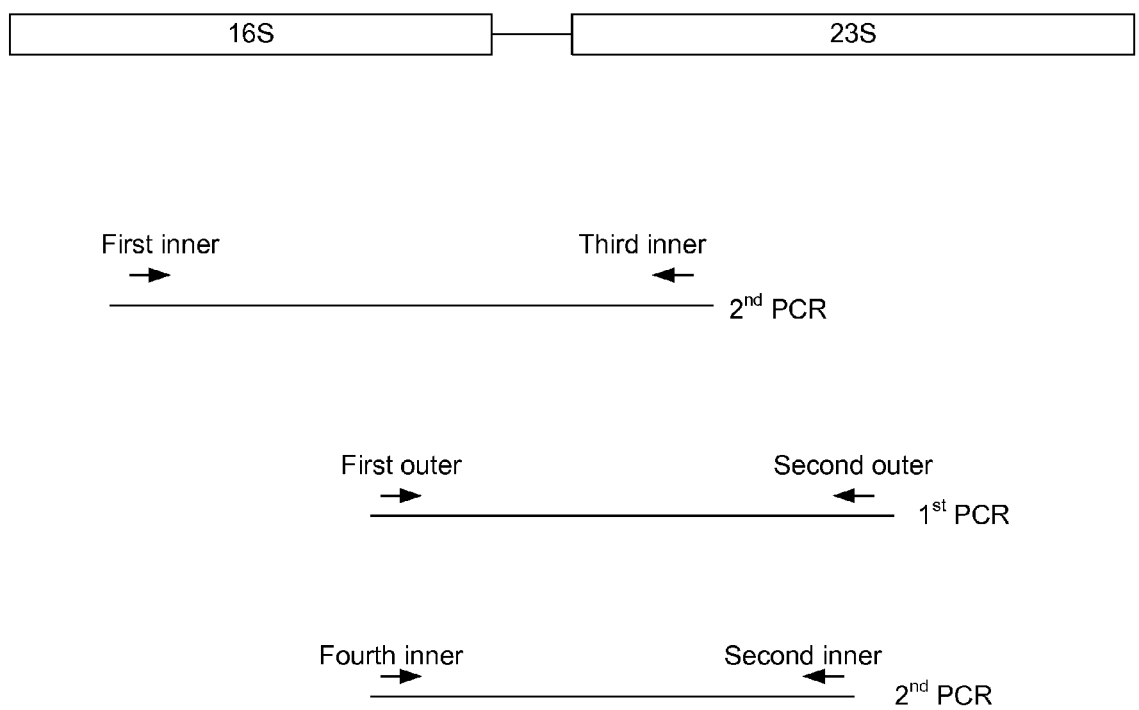
FIG. 2 is a schematic representation illustrating a nested PCR according to the present invention.

The at least two outer oligonucleotide primers may comprise an oligonucleotide sequence selected from the group consisting of 5'-GGATTAGATACCCTGGTAGTC-3' (SEQ ID NO:1) and 5'-GGAGTATTTAGCCTT-3' (SEQ ID NO:2). As shown in FIG. 2, for example, a first outer primer and a second outer primer may be used to generate the first amplified product. The first outer primer may comprise the forward primer of the 16S rRNA region, the first outer primer being about 785 bases from the 5'-end of the 16S region. The second outer primer may comprise the reverse primer of the 23S region, the second outer primer being about 422 bases from the 5'-end of the 23S region. As discussed below, the reaction mixture comprising the target nucleotide sequence and the first and second outer oligonucleotide primers may then be subject to PCR amplification.

Figure 4:
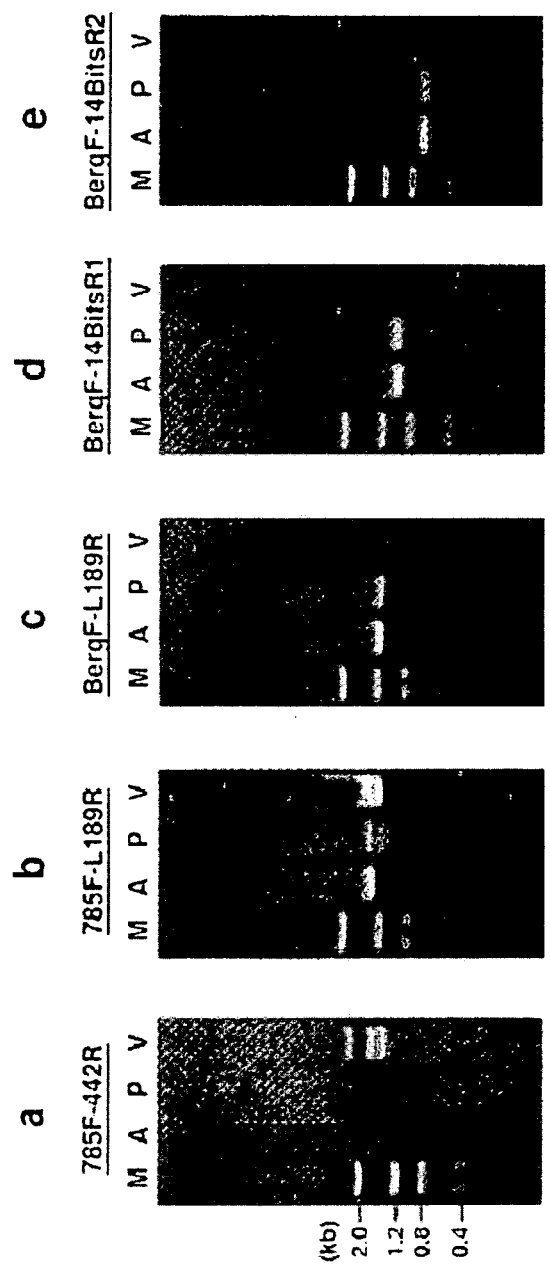
FIGS. 4A-E are a series of agarose gels showing direct and nested PCR analyses of samples collected from patient 14.

PCR amplification may be conducted on the reaction mixture using a temperature program and for a number of thermal cycles sufficient to amplify the target nucleotide sequence of the bacterial pathogen, if present. The PCR amplification can be carried out in any commercially available PCR thermal cycling apparatus, such as an Applied Biosystems 2720 thermal cycler (Applied Biosystems, Foster City, Calif.). For example, PCR may be carried out using a temperature resistant, DNA-dependent DNA polymerase, such as ACCUPRIME Taq DNA polymerase (Invitrogen, Carlsbad, Calif.). A total of about 1 µl of the extracted DNA may be used as the template in a total reaction volume of about 25 µl. The conditions for the PCR may be as follows: an initial denaturing at about 94° C. for about 3 minutes; about 25 to 27 cycles of denaturing at 94° C. for about 1 minute; annealing at about 42° C. for about 2 minutes; extension at about 72° C. for about 3 minutes; and an additional extension at about 72° C. for about 10 minutes. The resultant first amplified product may comprise at least a portion of the 16S-23S rRNA region and, as discussed in more detail below, be confirmed using agarose gel electrophoresis, for example (FIG. 4A).

It will be appreciated by one of ordinary skill in the art that the PCR amplification may also be performed using rapid temperature cycling techniques. Rapid temperature cycling techniques use a high surface area-to-volume sample container, such as a capillary tube, to contain the reaction amplification sample. The use of a high surface-area-to-volume sample container allows for rapid temperature response and temperature homogeneity throughout the sample. Rapid temperature cycling is contrasted to conventional temperature cycling in that 30 cycles of amplification can be completed in 15 minutes and the resulting PCR amplification products contain fewer side products. With rapid temperature cycling techniques, the required times for amplification are reduced approximately ten-fold and reaction specificity is improved.

After the presence of the first amplified product is confirmed, an appropriate volume of the initial reaction mixture (i.e., containing the first amplified product) may be subject to nested PCR. For example, an aliquot of about 5 µl of the initial reaction mixture may be treated with a reagent, such as Exo/SAP-IT (USB Co., Cleveland, Ohio) to remove single-stranded DNA (i.e., the at least two outer primers) from the aliquot. Next, an aliquot of about 1 µl from the treated reaction mixture may be used as the DNA template for the nested PCR. The conditions of the nested PCR may be identical to the conditions of the initial PCR described above, except that the annealing step may be performed at about 52° C.

The nested PCR may be performed using at least two inner oligonucleotide primers complementary or substantially complementary to the nucleotide sequence of the first amplified product so that a second amplified product is obtained. The at least two inner oligonucleotide primers may be selected from the group of primers consisting of 5'-GGATTA-GATACCCTGGTAGTC-3' (SEQ ID NO:1), 5'-GTTTGATC-CTGGCTCAG-3' (SEQ ID NO:3), 5'-GGTACTTAGAT-GTTTCAGTTC-3' (SEQ ID NO:4), and 5'-(G/T)TTCGCTCGCC(A/G)CTAC-3' (SEQ ID NO:5). PCR may then be performed as described above using a desired combination of the at least two inner oligonucleotide primers.

As shown in FIG. 2, for example, first and third inner oligonucleotide primers may be used for the nested PCR. The first inner oligonucleotide primer may comprise a forward primer of the 16S region, the first inner oligonucleotide primer being about 17 bases from the 5'-end of the 16S region. The third inner oligonucleotide primer can comprise a reverse primer of the 16S region, the third inner oligonucleotide primer being about 1,512 bases from the 5'-end of the 16S region. Subjecting the first and third inner oligonucleotide primers to the nested PCR may generate a second amplified product comprising at least a portion of the 16S rRNA region.

As also shown in FIG. 2, second and fourth inner oligonucleotide primers may additionally or optionally be used for the nested PCR. The second inner oligonucleotide primer can comprise a reverse primer of the 23S region, the second inner oligonucleotide primer being about 189 bases from the 5'-end of the 23S region. The fourth inner oligonucleotide primer can comprise a forward primer of the 16S region, the fourth inner oligonucleotide primer being about 785 bases from the 5'-end of the 16S region. Subjecting the second and fourth inner oligonucleotide primers to the nested PCR may generate a second amplified product comprising at least a portion of the 16S-23S rRNA region.

After conducting the nested PCR, the second amplified product may be detected at 16, if present. Methods for detecting amplified nucleic acids are well known in the art and can include, for example, agarose gel electrophoresis. In general, agarose gel electrophoresis is used to separate nucleic acid molecules based on their respective sizes. Separation of nucleic acids is generally achieved by moving the negatively charged molecules through an agarose matrix with an electric field such that shorter molecules move faster and migrate further through the gel than do longer ones. Various dyes are commonly used to assist in visualizing the nucleic acids in the gel. One example of such a dye, ethidium bromide, assists in visualizing the nucleic acids because it fluoresces under UV light when intercalated into DNA (or RNA). By running DNA through an ethidium bromide-treated gel and then visualizing the gel with UV light, distinct bands of DNA may be detected. As shown in FIG. 4B, for example, the second amplified product may be detected at 16 using an ethidium bromide-treated 1% agarose gel.

In another aspect of the present invention, the bacterial pathogen may be identified after detecting the second amplified product at 16. Methods for identifying a particular bacterial pathogen (i.e., the bacterial species) based upon amplified nucleic acid sequences are known in the art and include, for example, DNA cloning and sequencing techniques. In general, DNA cloning is a technique used to reproduce DNA fragments. It can be achieved by two different approaches: (1) cell-based; and (2) using PCR. In the cell-based approach, a vector (e.g., a plasmid), which typically contains an antibiotic-resistance gene, is used to carry the DNA fragment of interest into a host cell (e.g., a bacterial cell). In a process known as transformation, the recombinant DNA enters into the host cell and proliferates. A specific antibiotic is then added to kill any host cells which have not been transformed with the recombinant DNA and thus, any surviving host cells contain the DNA fragment of interest.

According to another aspect of the present invention, the second amplified product may be cloned into a suitable vector, such as the pCR2.1 vector, using a commercially available kit (e.g., TOPO TA cloning kit (Invitrogen)) and then transformed into a suitable host cell, such as DN5α E. coli cells. DNA may then be isolated from the surviving transformants using known DNA purification techniques and/or systems, such as the WIZARD PLUS SV miniprep system (Promega, Madison, Wis.).

After successfully isolating DNA from the transformants, DNA sequencing may be performed by using, for example, at least two oligonucleotide detection primers selected from the group consisting of 5'-GTAAAACGACGGCCAGT-3' (SEQ ID NO:6) and 5'-CAGGAAACAGCTATGAC-3' (SEQ ID NO:7) (Table 1). Techniques for sequencing DNA are known in the art and include, for example, chain termination and dye terminator sequencing methods.

The sequenced DNA may be searched and compared against known DNA sequences of bacterial pathogens using publicly available databases, such as GenBank, for example. Based on the degree of homology between the sequenced DNA and sequence information available from the database, a determination may be made as to the particular species (and genus) of the bacterial pathogen. From this information, it may then be possible to determine an appropriate therapeutic regimen for the subject, e.g., an appropriate course of antibiotic treatment.

In another aspect of the present invention, a kit is provided for detecting a bacterial pathogen in a sample. The kit can comprise at least two outer oligonucleotide primers complementary or substantially complementary to a target nucleotide sequence, such as a portion of the 16S-23S rRNA or 16S rRNA sequence of the bacterial pathogen. The at least two outer oligonucleotide primers may be selected from the group consisting of 5'-GGATTAGATACCCTGGTAGTC-3' (SEQ ID NO:1) and 5'-GGAGTATTTAGCCTT-3' (SEQ ID NO:2). The at least two outer oligonucleotide primers may be used with PCR under conditions identical or substantially identical to those described above to generate a first amplified product.

The kit may further comprise at least two inner oligonucleotide primers complementary or substantially complementary to the nucleic acid sequence of the first amplified product. The at least two inner oligonucleotide primers may be selected from the group consisting of 5'-GGATTAGATAC-CCTGGTAGTC-3' (SEQ ID NO:1), 5'-GTTTGATCCTG-GCTCAG-3' (SEQ ID NO:3), 5'-GGTACTTAGAT-GTTTCAGTTC-3' (SEQ ID NO:4), and 5'-(G/T)TTCGCTCGCC(A/G)CTAC-3' (SEQ ID NO:5). The at least two inner oligonucleotide primers may be used with a nested PCR under conditions identical or substantially identical to those described above to generate a second amplified product. The second amplified product may then be used to detect the presence or absence of the bacterial pathogen using known detection methods (e.g., agarose gel electrophoresis), such as those described above.

It will be appreciated that the kit may also include other reagents needed to detect the bacterial pathogen. Because the kit may be used with PCR, other reagents that may be included with the kit are temperature resistant, DNA-dependent DNA polymerases, deoxynucleotide triphosphates, and other known reaction buffers. It will also be appreciated that the kit may include at least two detection oligonucleotide primers for identifying the bacterial pathogen (as described above). The at least two detection oligonucleotide primers can include oligonucleotides selected from the group consisting of 5'-GTAAAACGACGGCCAGT-3' (SEQ ID NO:6) and 5'-CAGGAAACAGCTATGAC-3' (SEQ ID NO:7). Further, it will be appreciated that the kit may include one or more enclosures (e.g., boxes) containing the relevant reaction reagents and/or supporting materials for assays of the present invention, such as reagents needed to perform DNA cloning and/or sequencing.

The following examples are for the purpose of illustration only and are not intended to limit the scope of the claims, which are appended hereto.

EXAMPLE 1

Study Population and Sample Collection

The study was approved by the Internal Review Board at the MetroHealth Medical Center (MHMC) in Cleveland, Ohio. A total of 35 pregnant women undergoing transabdominal amniocentesis at the Fetal Diagnostic Center or the Labor and Delivery Department at MHMC were recruited. Women who were pregnant with multiple fetuses, who were more than 5 cm dilated, or whose fetal membranes were ruptured and who had been on antibiotics within 2 weeks prior to amniocentesis were excluded from the study. Qualified patients were requested to sign a written consent and to fill out a questionnaire. Additional information was obtained from the patient's medical record. Three samples were collected at the time of recruitment: AF, blood, and vaginal swabs. Following amniocentesis, AF was placed directly into sterile 15-ml Corning centrifuge tubes (Corning Inc., Corning, N.Y.). The vaginal samples were collected from the lower two-thirds of the vagina by using the S/P brand culture swab collection and transport system (Allegiance Healthcare, McGraw Park, Ill.), aided by a sterile speculum for visualization. The subgingival plaque samples were collected either at MHMC at the time of recruitment or later at the School of Dental Medicine at Case Western Reserve University. Full-mouth subgingival plaque was collected using sterile curettes and pooled into 2 ml sterile phosphate buffer (Sigma, St. Louis, Mo.). Caution was taken during sample collection to avoid traumatizing the soft tissue. All samples were placed into a PackAnaero system (Mitsubishi Gas Chemical Inc., New York, N.Y.) within 10 to 15 min of collection and transported to the laboratory. The blood was cultured immediately for bacterial growth. AF samples were divided into 1-ml aliquots. The vaginal swabs were suspended in sterile phosphate-buffered saline. All samples were then centrifuged at 10,000×g for 3 min. The supernatants were removed, and the pellets were stored at −80° C. The placenta was submitted to the Pathology Department at MetroHealth Medical Center for pathological examination. A total of six tissue blocks, including two sections each of umbilical cord and membranes and four full-thickness sections of placental parenchyma, were prepared. Hematoxylin- and eosin-stained slides of these blocks were later examined.

TABLE 2

Summary of pertinent medical records and sample collection

| | | Hospital diagnosis of AF[b] | | | | Gestation time (wk) at: | | |
| --- | --- | --- | --- | --- | --- | --- | --- | --- |
| Patient No. | Reason for amniocentesis* | Culture | Gram Stain | Glucose (mg/dl) | WBC (ml) | Amniocentesis | Delivery | Samples obtained* |
| 1 | PTL | — | — | 37 | 13 | 34 | 35 | A, B, P, V |
| 2 | PTL | — | — | 24 | 7 | 32 | 32 | A, B, P, V |
| 3 | PTL | — | — | 56 | 16 | 22 | 25 | A, B, V |
| 4 | PTL | — | — | 19 | 15 | 32 | 36 | A, B, P, V |
| 5 | PTL | — | — | 17 | 36 | 21 | 25 | A, B, P, V |
| 6 | PTL | — | — | 54 | 5 | 28 | 36 | A, B, P, V |
| 7 | PTL | — | — | 50 | NA[d] | 33 | 35 | A, B, V |
| 8 | PTL | — | — | 32 | 3 | 18 | 33 | A, B, V |
| 10 | PTL | — | — | NA | NA | 32 | 34 | A, B, V |
| 14 | PTL | — | — | <3 | 3,304 | 24 | 24 | A, B, P, V |
| 15 | PTL | — | — | 49 | 13 | 32 | 32 | A, B, P, V |
| 16 | PTL | — | — | 65 | 13 | 32 | 33 | A, B, P, V |
| 20 | PTL | — | — | 21 | 18 | 20 | 33 | A, B, V |
| 22 | PTL | — | — | NA | 2 | 33 | NA[e] | A, B, V |
| 24 | PTL | — | — | 34 | 40 | 21 | 27 | A, B, V |
| 28 | PTL | — | — | NA | 2 | 31 | 38 | A, B, V |
| 31 | PTL | — | — | 21 | 5 | 22 | 23 | A, B, P, V |
| 32 | PTL | — | — | 29 | 12 | 33 | 33 | A, B, V |
| 33 | PTL | — | — | 37 | 10 | 24 | 38 | A, B, V |
| 9 | Lung | NA | NA | NA | NA | 36 | 36 | A, B, V |
| 11 | Lung | NA | NA | NA | NA | 34 | 35 | A, B, V |
| 18 | Lung | NA | NA | NA | NA | 36 | 37 | A, B |
| 21 | Lung | NA | NA | NA | NA | 36 | 38 | A, B, P, V |
| 23 | Lung | NA | NA | NA | NA | 36 | 37 | A, B, P, V |
| 25 | Lung | NA | NA | NA | NA | 36 | 37 | A, B, P, V |
| 26 | Lung | NA | NA | NA | NA | 36 | 38 | A, B, V |
| 27 | Lung | NA | NA | NA | NA | 35 | 35 | A, B, V |
| 29 | Lung | — | — | 46 | 4 | 34 | 35 | A, B, V |
| 34 | Lung | NA | NA | NA | NA | 35 | 35 | A, B, V |
| 35 | Lung | NA | NA | NA | NA | 36 | 36 | A, B, V |
| 12 | NA | NA | NA | NA | NA | 21 | 40 | A, B, V |
| 13 | NA | NA | NA | NA | NA | 17 | NA[e] | A, B, V |

TABLE 2-continued

Summary of pertinent medical records and sample collection

| Patient No. | Reason for amniocentesis[a] | Hospital diagnosis of AF[b] | | | | Gestation time (wk) at: | | Samples obtained[c] |
|---|---|---|---|---|---|---|---|---|
| | | Culture | Grain Stain | Glucose (mg/dl) | WBC (ml) | Amniocentesis | Delivery | |
| 17 | NA | NA | NA | NA | NA | 25 | 40 | A, B, V |
| 30 | NA | NA | NA | NA | NA | 24 | 25 | A, B, P, V |

[a]The reason for amniocentesis include preterm labor or threatening preterm labor, including cervical incompetence (PTL); checking for fetal lung maturity (Lung); and fetal genetic diagnosis (Genet.).
[b]Tests of the AF were performed at the hospital laboratory. The results were obtained from the patient's medical records.
[c]A, AF; B, blood; P, subvaginal plaque; V vaginal swab
[d]NA not available.
[e]The patient did not deliver at MHMC.

DNA Extraction

Each frozen sample pellet was suspended in 500 µl lysis buffer (50 mM Tris-HCl, pH 8.0, 500 mM NaCl, 50 mM EDTA, 1% sodium dodecyl sulfate) containing 150 mg of 0.1-mm and 50 mg of 0.5-mm zirconia/silica beads (Biospec Products, Inc., Bartlesville, Okla.). Samples were vigorously mixed for 3 min by vortexing and incubated at 70° C. for 15 min. After centrifugation at 10,000×g for 5 min, the supernatant was collected and mixed with 130 µl of 10 M ammonium acetate. The mixture was incubated on ice for 5 min and centrifuged at 10,000×g for 10 min. DNA was isolated from the supernatant by isopropanol precipitation, purified using a GeneClean Turbo kit (Qbiogene, Irvine, Calif.), and suspended in 30 µl of elution solution from the kit.

Amplification of the Ribosomal 16S-23S rRNA Gene Region

All PCRs were carried out using AccuPrime Taq DNA polymerase (Invitrogen, Carlsbad, Calif.) and an Applied Biosystems 2720 thermal cycler (Applied Biosystems, Foster City, Calif.). A total of 1 µl of DNA from each sample was used as the template in a 25-µl reaction volume. Following the first PCR, an aliquot of 5 µl of the reaction mixture was treated with 2 µl of Exo/SAP-IT (USB Co., Cleveland, Ohio) following the manufacturer's instruction. An aliquot of 1 µl from the Exo/SAP-IT reaction mixture was then used as the DNA template for the nested PCR. The conditions of PCR were as follows: an initial denaturing at 94° C. for 3 min; 25 to 27 cycles of denaturing at 94° C. for 1 min, annealing at 42° C. (or at 52° C. for nested PCR) for 2 min, and extension at 72° C. for 3 min; and an additional extension at 72° C. for 10 min. Primers used for PCR are listed in Table 1. Primer BergF is complementary to the Bergeyella-specific primer kindly provided by Bruce Paster. Primers 14 BitsR1 and 14 BitsR2 were designed based on the DNA sequence of the highly variable internal transcribed spacer (ITS) region between the 16S and 23S rRNA genes of the Bergeyella sp. clone AF14. The PCR products were examined by 1% agarose gel electrophoresis.

TABLE 1

Primers used in this study

| Primer | Description | Sequence (5'-3') | Reference of Source |
|---|---|---|---|
| A17F | Forward primer in 16S region, 17 bases from 5' end | GTTTGATCCTGGCTCAG (SEQ ID NO: 3) | 25 |
| 785F | Forward primer in 16S region, 785 bases from 5' end | GGATTAGATACCCTGGTAGTC (SEQ ID NO: 1) | 25 |
| 422R | Reverse primer in 23S region, 422 bases from 5' end of 23S | GGAGTATTTAGCCTT (SEQ ID NO: 2) | 25 |
| L189R | Reverse primer in 23S region, 189 bases from 5' end of 23S | GGTACTTAGATGTTTCAGTTC (SEQ ID NO: 4) | 25 |
| 1512R | Reverse primer in 16S region, 1,512 bases from 5' end of 16S | TACCTTGTTACGACTT (SEQ ID NO: 8) | 25 |
| BergF | Forward primer for Bergeyella spp., 1,000 bases from 5' end of 16S | GACAGCTGTAGAAATACGG (SEQ ID NO: 9) | This study |
| 14BitsR1 | Reverse primer for ITS region of Bergeyella clone AF14B | TCAGCACTCGAAAGTGCTCGG (SEQ ID NO: 10) | This study |
| 14BitsR2 | Reverse primer for ITS region of Bergeyella clone AF14B | CTTAGTCTCTATTAATCCCTG (SEQ ID NO: 11) | This study |
| M13 Universal (-21) | For DNA sequencing | GTAAAACGACGGCCAGT (SEQ ID NO: 6) | MBC[a] |

TABLE 1-continued

Primers used in this study

| Primer | Description | Sequence (5'-3') | Reference of Source |
|---|---|---|---|
| M13-2 Reverse | For DNA sequencing | CAGGAAACAGCTATGAC (SEQ ID NO: 7) | MBC |

[a]MBC, Molecular Biotechnology Core, Lerner Institute, Cleveland, Ohio.

DNA Cloning and Sequencing

The PCR products were cloned into the pCR2.1 vector by use of a TOPO TA cloning kit (Invitrogen) according to the manufacturer's instructions. Plasmid DNA was isolated from the transformants by using a Wizard Plus SV Minipreps DNA purification system (Promega, Madison, Wis.). The plasmid DNA was sequenced at the Molecular Biotechnology Core (Lerner Research Institute, Cleveland, Ohio) using sequencing primers M13 Universal (-21) and M13-2 Reverse (Table 1).

Nucleotide Sequence Accession Number

The 2,375-bp nucleotide sequence of the 16S rRNA gene, the complete ITS region, and the 5'-end portion of the 23S rRNA gene of *Bergeyella* sp. clone AF14 has been deposited in the GenBank database with accession number DQ241813.

EXAMPLE 2

Study Population, Sample Collection, and Medical Data Collection

A total of 35 women pregnant with singletons and undergoing transabdominal amniocentesis were recruited at MHMC. One patient (patient 19) was excluded from the study due to an error in sample collection. For the remaining 34 patients, the population consisted of 50.0% African-American, 35.3% Caucasian, and 14.7% Hispanic subjects, with an average age of 26.6 years. On the basis of the reasons for amniocentesis, the patients were divided into three groups: group 1, patients in preterm labor (PTL) or threatening PTL, including those undergoing cerclage due to an incompetent cervix (19 patients); group 2, patients checking for fetal lung maturity (11 patients); and group 3, patients interested in fetal genetic diagnosis (4 patients) (Table 2). The gestational ages at the times of amniocentesis and delivery were recorded, as were the samples collected from each patient (Table 2). Among group 1 patients, approximately 58% delivered before 35 weeks of gestation, with five delivering extremely early, before 30 weeks of gestation (patients 3, 5, 14, 24, and 31). The rates of premature delivery before 35 weeks were lower in groups 2 and 3, at 0% and 25%, respectively, with only one case of extremely early delivery in group 3 (patients 9 and 30) (Table 2).

For group 1, hospital laboratory diagnosis of infection in the AF was ordered by the attending physicians. The results of these tests were obtained retrospectively from the patients' medical records (Table 2). No such tests were usually ordered for patients in groups 2 and 3 (Table 2). No bacteria were detected in the AF of any patients by either culturing or Gram staining. Most patients showed a normal glucose concentration in AF, ranging from 17 to 65 mg/dl, and a normal white blood cell (WBC) count of 2 to 40 cells/ml. One patient (patient 14), however, showed abnormal results, with a decreased glucose concentration of ~3 mg/dl, below the diagnosis criteria of 5 mg/dl (24), as well as an elevated WBC of 3,304 cells/ml with approximately 90% neutrophils. This patient was admitted to the hospital due to premature contractions. Amniocentesis was performed because she did not respond to tocolysis and her cervix continued to dilate to 3 to 4 cm. Results of AF tests indicated intrauterine infection despite the lack of detection of bacteria in the amniotic fluid. On the basis of this diagnosis, patient 14 was induced immediately, at 24 weeks of gestation, and delivered a female infant weighing 1 lb 7 oz. The infant was sent to the neonatal intensive care unit and survived. Following delivery, the patient's placenta was sent for pathological examination, which revealed necrotizing acute and chronic chorioamnionitis with a diffuse fetal inflammatory response in all umbilical and chorionic plate vessels and umbilical cord stroma, further confirming the intrauterine infection.

Analysis of Blood and AF Samples

Figure 3:
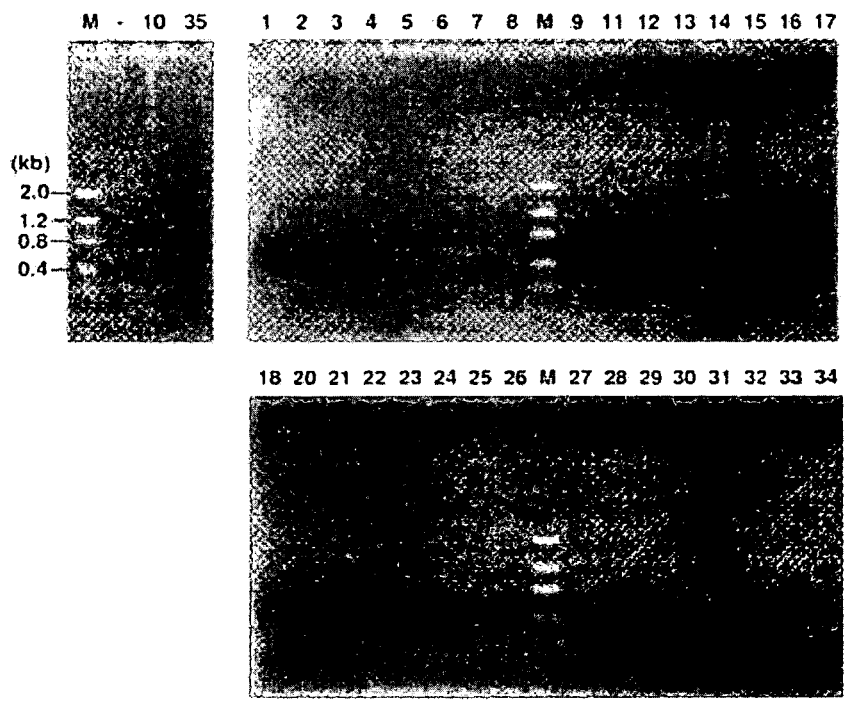
FIG. 3 is a series of agarose gels showing PCR examination of amniotic fluid samples with universal primers 785F and 442R. The numbers at the top of correspond to patient number. Lane M, DNA molecular size markers, as indicated on the left; Lane –, negative control.

The blood samples collected from the 34 patients were cultured anaerobically at 37° C. for 1 to 2 weeks. No bacterial growth was detected in any samples. The AF samples were analyzed by PCR using universal primers 785F and 422R. Using a lab working strain, *Fusobacterium nucleatum* 12230, as a testing organism, the limit of detection by this approach was determined to be 106 CFU (data not shown). Bacteria were detected only in patient 14 (FIG. 3). Thus, patient 14 likely had an AF infection with a significant bacterial titer, consistent with the severe intrauterine infection diagnosed clinically. The other patients were either not infected or infected at a subclinical level not detected by PCR.

The 1,602-bp fragment amplified from patient 14 by PCR was cloned into pCR2.1, and the DNA sequences from 10 independent clones were determined. The sequences were 99.8% to 100% identical to each other, with only one or two random changes occurring at different positions in different clones, likely caused by infidelities of PCR (data not shown). When the consensus sequence derived from these 10 clones was searched against the NCBI nucleotide database, the first 709 bp, corresponding to the 3'-end region of the 16S rRNA gene, matched 99.8% with the corresponding sequences from an uncultivable oral strain, *Bergeyella* sp. clone AK152, deposited by B. J. Paster et al. (accession number AY008691). The remaining DNA sequence on the 1,602-bp fragment, containing ITS and 5'-end 23S rRNA sequences, could not be matched because there was no DNA sequence available from *Bergeyella* sp. clone AK152 in that region (FIG. 2).

In order to compare DNA sequences of the 5' ends of 16S rRNA, AF from patient 14 was analyzed by nested PCR using primers A17F and 1512R (FIG. 2 and data not shown). The limit of detection by nested PCR was 10 CFU, as determined using *F. nucleatum* 12230 as a testing organism (data not shown). The fragments amplified by nested PCR were cloned, and the sequences from three independent clones were determined. Again, only *Bergeyella* was detected. When the DNA sequences of the entire 1,482 bp of the 16S rRNA gene were compiled and aligned against those from *Bergeyella* sp. Clone AK152, a total of five mismatches were detected. With a 99.7% match of the 16S rRNA, it is apparent that the intrauterine infection of patient 14 was caused predominantly by an oral *Bergeyella* strain, designated clone AF14. This strain differs from the type species *Bergeyella zoohelcum* because they share only 87 to 92% identity at the 16S rRNA level.

Examination of the Subgingival Plaque and Vaginal Swab of Patient 14

To determine the source of intrauterine *Bergeyella* infection in patient 14, her subgingival plaque and vaginal swab samples were analyzed by nested PCR. The first PCR using universal primers 785F and 442R detected bacteria in both samples, with more in the vaginal swab than in the subgingival plaque (FIG. 4A). This observation verified the adequacy of sample collection, which was further confirmed by nested PCR using universal primers 785F and L189R (FIG. 4B). Nested PCR using a *Bergeyella*-specific primer, BergF, and the universal primer L189R amplified a strong 1,168-bp fragment from both AF and subgingival plaque but not from the vaginal sample (FIG. 4C). Similar results were observed with two additional nested PCRs, using all *Bergeyella*-specific primers, i.e., BergF-14 BitsR1 and BergF-14 BitsR2. *Bergeyella*-specific fragments of 961 bp and 648 bp were amplified from AF and subgingival plaque but not from the vaginal swab (FIGS. 3D-E).

All three fragments (1,168, 961, and 648 bp) amplified from the subgingival plaque of patient 14 were then cloned into pCR2.1, followed by DNA sequence analysis. A total of 28 independent clones were sequenced. For each of the three fragments, two groups of sequences were identified, with one matching exactly that from AF and the other matching by 99.0 to 99.7% (data not shown). The sequence variations in the second group could be due to the increased infidelity of nested PCR; alternatively, they could indicate different strains of *Bergeyella* or different 16S-23S rRNA operons of the same strain. In either case, since the *Bergeyella* sequences identified in AF matched those in the subgingival plaque and since no *Bergeyella* was detected in the patient's lower vaginal tract, it is plausible that *Bergeyella* sp. clone AF14 originated from her oral cavity rather than from the vagina.

Detection of *Bergeyella* in the Subgingival Plaque of Women without Intrauterine Infection

Figure 5:
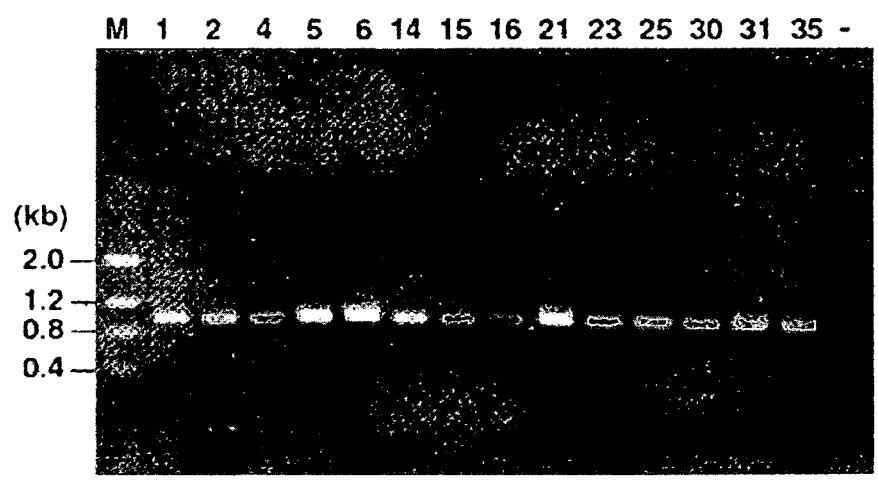
FIG. 5 is an agarose gel showing detection of Bergeyella in subgingival plaque samples by nested PCR using primers BergF and 14 BitsR1. The numbers on the top correspond to the patient numbers. Lane M, DNA molecular size markers, as indicated on the left. Lane –, negative control.

*Bergeyella* was detected in the subgingival plaque of all 14 patients tested by nested PCR using BergF and 14 BitsR1 (FIG. 5) and BergF and 14 BitsR2 (data not shown). However, patient 14 was the only subject positive for *Bergeyella* in AF.

From the above description of the invention, those skilled in the art will perceive improvements, changes and modifications. Such improvements, changes and modifications within the skill of the art are intended to be covered by the appended claims.

Having described the invention, the following is claimed:

1. A method for detecting a bacterial pathogen in amniotic fluid, the method comprising the steps of:
   obtaining a sample of the amniotic fluid;
   subjecting the sample to nested PCR;
   wherein the nested PCR is conducted in the presence of at least two outer oligonucleotide primers complementary to a target nucleotide sequence of the bacterial pathogen so that a first amplified product is produced, the target nucleotide sequence spanning between at least a portion of a 16S and 23S ribosomal RNA sequence;
   wherein the first amplified product spanning between at least a portion of a 16S and 23S ribosomal RNA sequence is subject to the nested PCR in the presence of at least two inner oligonucleotide primers complementary to the nucleotide sequence of the first amplified product so that a second amplified product is obtained; and
   detecting the second amplified product, wherein the second amplified product indicates the presence of the bacterial pathogen in the sample, wherein the at least two outer oligonucleotide primers being selected from the group consisting of 5'-GGATTAGATACCCTGGTAGTC-3' (SEQ ID NO:1) and 5'-GGAGTATTTAGCCTT-3' (SEQ ID NO:2).

2. The method of claim 1, the at least two inner oligonucleotide primers being selected from the group consisting of 5'-GGATTAGATACCCTGGTAGTC-3' (SEQ ID NO1), 5'-GTTTGATCCTGGCTCAG-3' (SEQ ID NO:3), 5'-GGTACTTAGATGTTTCAGTTC-3' (SEQ ID NO:4), and 5'-(G/T)TTCGCTCGCC(A/G)CTAC-3' (SEQ ID NO:5).

3. The method of claim 1 further comprising the step of identifying the bacterial pathogen corresponding to the second amplified product.

4. The method of claim 3, the step of identifying the bacterial pathogen including cloning the second amplified product into a construct and DNA sequencing conducted in the presence of at least two detection oligonucleotide primers selected from the group consisting of 5'-GTAAAACGACGGCCAGT-3' (SEQ ID NO:6) and 5'-CAGGAAACAGCTATGAC-3' (SEQ ID NO:7).

5. A method for detecting a bacterial pathogen in amniotic fluid, the method comprising the steps of:
  obtaining a sample of the amniotic fluid;
  subjecting the sample to nested PCR;
  wherein the nested PCR is conducted in the presence of at least two outer oligonucleotide primers complementary to a target nucleotide sequence of the bacterial pathogen so that a first amplified product is produced, the target sequence comprising at least a portion of a 16S ribosomal RNA sequence, an intergene region, and at least a portion of a 23S ribosomal RNA sequence, the at least two outer oligonucleotide primers being selected from the group consisting of 5'-GGATTAGATACCCTGGTAGTC-3' (SEQ ID NO:1) and 5'-GGAGTATTTAGCCTT-3' (SEQ ID NO:2);
  wherein the first amplified product is subject to the nested PCR in the presence of at least two inner oligonucleotide primers complementary to the nucleotide sequence of the first amplified product so that a second amplified product is obtained, the first amplified product comprises at least a portion of a 16S ribosomal RNA sequence, an intergene region, and at least a portion of a 23S ribosomal RNA sequence, the at least two inner oligonucleotide primers being selected from the group consisting of 5'-GGATTAGATACCCTGGTAGTC-3' (SEQ ID NO:1), 5'-GTTTGATCCTGGCTCAG-3' (SEQ ID NO:3), 5'-GGTACTTAGATGTTTCAGTTC-3' (SEQ ID NO:4), and 5'-(G/T)TTCGCTCGCC(A/G)CTAC-3' (SEQ ID NO:5), and
  detecting the second amplified product, wherein the second amplified product indicates the presence of the bacterial pathogen in the sample.

6. The method of claim 5 further comprising the step of identifying the bacterial pathogen corresponding to the second amplified product.

7. The method of claim 6, the step of identifying the bacterial pathogen including cloning the second amplified product into a construct and DNA sequencing conducted in the presence of at least two detection oligonucleotide primers selected from the group consisting of 5'-GTAAAACGACGGCCAGT-3' (SEQ ID NO:6) and 5'-CAGGAAACAGCTATGAC-3' (SEQ ID NO:7).

* * * * *

SEQUENCE LISTING

<160> NUMBER OF SEQ ID NOS: 11

<210> SEQ ID NO 1
<211> LENGTH: 21
<212> TYPE: DNA
<213> ORGANISM: Homo sapiens

<400> SEQUENCE: 1
ggattagata ccctggtagt c                                       21

<210> SEQ ID NO 2
<211> LENGTH: 15
<212> TYPE: DNA
<213> ORGANISM: Homo sapiens

<400> SEQUENCE: 2
ggagtattta gcctt                                              15

<210> SEQ ID NO 3
<211> LENGTH: 17
<212> TYPE: DNA
<213> ORGANISM: Homo sapiens

<400> SEQUENCE: 3
gtttgatcct ggctcag                                            17

<210> SEQ ID NO 4
<211> LENGTH: 21
<212> TYPE: DNA
<213> ORGANISM: Homo sapiens

<400> SEQUENCE: 4
ggtacttaga tgtttcagtt c                                       21

<210> SEQ ID NO 5
<211> LENGTH: 16
<212> TYPE: DNA
<213> ORGANISM: Homo sapiens

```
<400> SEQUENCE: 5
kttcgctcgc crctac                                                    16

<210> SEQ ID NO 6
<211> LENGTH: 17
<212> TYPE: DNA
<213> ORGANISM: Homo sapiens

<400> SEQUENCE: 6
gtaaaacgac ggccagt                                                   17

<210> SEQ ID NO 7
<211> LENGTH: 17
<212> TYPE: DNA
<213> ORGANISM: Homo sapiens

<400> SEQUENCE: 7
caggaaacag ctatgac                                                   17

<210> SEQ ID NO 8
<211> LENGTH: 16
<212> TYPE: DNA
<213> ORGANISM: Homo sapiens

<400> SEQUENCE: 8
taccttgtta cgactt                                                    16

<210> SEQ ID NO 9
<211> LENGTH: 19
<212> TYPE: DNA
<213> ORGANISM: Homo sapiens

<400> SEQUENCE: 9
gacagctgta gaaatacgg                                                 19

<210> SEQ ID NO 10
<211> LENGTH: 21
<212> TYPE: DNA
<213> ORGANISM: Homo sapiens

<400> SEQUENCE: 10
tcagcactcg aaagtgctcg g                                              21

<210> SEQ ID NO 11
<211> LENGTH: 21
<212> TYPE: DNA
<213> ORGANISM: Homo sapiens

<400> SEQUENCE: 11
cttagtctct attaatccct g                                              21
```